United States Patent
Chen

(10) Patent No.: US 9,983,145 B1
(45) Date of Patent: May 29, 2018

(54) TEST PROBE CARD DETECTION METHOD AND SYSTEM THEREOF

(71) Applicant: GLTTEK CO., LTD, Hsinchu (TW)

(72) Inventor: Chiung Nan Chen, Hsinchu (TW)

(73) Assignee: GLTTEK CO., LTD, Hsinchu (TW)

( * ) Notice: Subject to any disclaimer, the term of this patent is extended or adjusted under 35 U.S.C. 154(b) by 0 days. days.

(21) Appl. No.: 15/648,392

(22) Filed: Jul. 12, 2017

(51) Int. Cl.
G01N 21/00 (2006.01)
G01N 21/88 (2006.01)
G01N 21/95 (2006.01)

(52) U.S. Cl.
CPC ..... *G01N 21/8806* (2013.01); *G01N 21/8851* (2013.01); *G01N 21/95* (2013.01)

(58) Field of Classification Search
CPC .............. G01N 21/9501; G01N 21/94; G01N 21/8806; G01N 21/956; G01N 21/95607
USPC ...................................................... 356/237.2
See application file for complete search history.

(56) References Cited

U.S. PATENT DOCUMENTS

| | | | | |
|---|---|---|---|---|
| 5,800,184 A * | 9/1998 | Lopergolo | ........... | H05K 7/1069 439/591 |
| 6,292,003 B1 * | 9/2001 | Fredrickson | ......... | G01R 1/0483 324/750.25 |
| 6,710,798 B1 * | 3/2004 | Hershel | .............. | G01R 31/2887 324/750.23 |
| 8,078,256 B2 * | 12/2011 | Zan | ...................... | A61B 8/0833 219/218 |
| 9,684,052 B2 * | 6/2017 | Olmstead | ............... | G01R 35/00 |
| 2007/0096763 A1 * | 5/2007 | Ehrmann | ........... | G01R 31/2891 324/750.23 |
| 2008/0197865 A1 * | 8/2008 | Endres | ............... | G01R 31/2886 324/754.07 |
| 2010/0176831 A1 * | 7/2010 | Palcisko | ............ | G01R 1/07378 324/756.03 |
| 2011/0267087 A1 * | 11/2011 | Huang | ............... | G01R 31/2635 324/754.23 |
| 2014/0092716 A1 * | 4/2014 | Saito | ...................... | B82Y 35/00 369/53.38 |
| 2015/0177313 A1 * | 6/2015 | Hoelter | .............. | G02B 27/0977 324/754.21 |

FOREIGN PATENT DOCUMENTS

CN 102478385 A 5/2012
TW M418385 U1 12/2011

* cited by examiner

*Primary Examiner* — Md M Rahman
(74) *Attorney, Agent, or Firm* — Chun-Ming Shih

(57) ABSTRACT

A test probe card detection system includes a linear scanning lens module, a CCD microscope module, a CCD image adjustment module, and a computer. The CCD microscope module adjusts and confirms a scanning optical focal length of a test probe card to be tested. The linear scanning lens module scans all areas data of the test probe card and stores the scanned all areas data in a database. The all areas data is compared with a coordinate file in order to detect defected pins of the test probe card. The CCD microscope module confirms and obtains data of the detected defected pins of the test probe card. The data of the detected defected pins is sent to the CCD image adjustment module and are shown on the computer. The defected pins include pins having surface oxidation, wear, damage, and breaking; lacking of pins; and deflected pins.

9 Claims, 7 Drawing Sheets

TEST PROBE CARD DETECTION METHOD AND SYSTEM THEREOF

BACKGROUND OF THE INVENTION

1. Technical Field

The technical field relates to a test probe card detection method and system thereof, and more particularly relates to a test probe card detection method and system thereof capable of fully automatically detecting defected pins, wear, oxidation, breaking, lacking of pins, and deflected pin of the test probe card.

2. Description of Related Art

Conventional test probe card detection apparatus includes a fastening device for securing a test probe card onto a platform. A location indicator is provided on the platform for simulating each pin pad of a wafer. A microscope is used to observe the pin location of the test probe card in order to confirm whether it complies with the location of each pin pad. Further, a display of a computer shows it. The test probe card is manually taken out of the platform to an adjustment device for adjusting the pin to a correct location if the observed pin location of the test probe card does not comply with the corrected location of the pin pad.

The detection method involves dividing all pin areas of a test probe card into a plurality of areas to be tested, and detecting each area sequentially. However, the observation and the adjustment of the test probe card are done in different devices. Thus, the test probe card is required to manually move to different devices in different steps. It is very tedious. Further, it is required to record a sequence of areas to be tested in the detection method. Repetition or omission of certain area is possible if there is no correct record. This is a waste. It also has the problem of low yield.

For solving above drawbacks, Taiwan Utility Model Number M418,385 discloses a test probe card detection device having the following characteristics. A platform for placing a test probe card to be tested thereon is provided. The platform move along x-axis or y-axis. An image fetching unit such as a digital camera is provided for fetching pin location of the test probe card. A microscope unit is provided for observing displaced pin. A control unit is provided for controlling movement of the platform on each of the image fetching unit and the microscope unit. In a detection step, the test probe card is divided into a plurality of areas A to be tested. Image of each area is fetched sequentially. Embedded measurement software is then executed to determine whether the pin location is correct or not. The platform moves the test probe card having incorrect pin location to the microscope unit for further observation and adjustment.

While the utility model patent can eliminate the conventional drawbacks including manually detaching the test probe card and mounting same on an adjustment device for adjustment, it has the following problems to be solved:

The test probe card is required to divide into a plurality of areas, and each area is required to take an image for sequential comparison. There are tens of thousands of pins. Thus, its operation is very tedious and omission is possible. Further, it is time consuming. For example, detection time for a test probe card is about 40 minutes.

The comparison of areas is taken sequentially (i.e., one by one). There is movement error for each comparison and the error is accumulated. As a result, the subsequent comparison has a greatly increased error and low precision.

Four points positioning is implemented. An error of one point may cause each pin to have an error. That is, all pins have error. As a result, the collected measurement data is erroneous due to incorrect point positioning.

Light is emitted in an annular shape in measurement. However, such light can shade surfaces of a defected pin. For example, surface oxidation or wear of a pin can cause the pin to be blurry. Hence, it is neither possible of detecting defected surfaces (e.g., oxidation or wear) of a pin nor possible of detecting breaking of a pin and lacking of pins. The utility model patent only can detect a deflected pin.

A microscope is used in pin adjustment. A mask or negative is required to as a basis for positioning. However, the positioning is laborious and time consuming. Further, the pin adjustment is completely done manually. There is no basis for determining the adjustment is correct or not. It completely depends upon the feeling of the employee operating the device. Hence, its correctness is not reliable. Precision of repeatedly adjusting a pin is very low.

China Patent Number CN102478385A discloses a test probe card detection method and system thereof. The Chinese Invention Patent has characteristics substantially the same as the Taiwanese Utility Model Patent and thus has the same drawbacks.

Thus, the need for improvement still exists.

SUMMARY OF THE INVENTION

The disclosure is directed to a test probe card detection method and system thereof for solving above problems of the conventional art.

It is therefore one object of the invention to provide a test probe card detection system comprising an x-y axis movement platform configured to move in Cartesian coordinates (x, y) with the test probe card to be tested placed on the x-y axis movement platform; a linear scanning lens module disposed above the x-y axis movement platform in movement, the linear scanning lens module configured to move along z-axis in a three dimensional Cartesian coordinate system, and the linear scanning lens module configured to obtain image data of all area of the test probe card to be tested by scanning; a CCD microscope module disposed above the x-y axis movement platform in movement, the CCD microscope module configured to move along z-axis in a three dimensional Cartesian coordinate system; a CCD image adjustment module disposed above the x-y axis movement platform in movement, the CCD image adjustment module configured to move along z-axis in a three dimensional Cartesian coordinate system; and a computer including an operation module, an input and output module, and a database wherein the database is configured to store data including data of a test probe card coordinate file, the input and output module is configured to input instructions and output graphic and text files, and the operation module is configured to process input and output information; wherein the computer controls the x-y axis movement platform to move the test probe card to be tested, the CCD microscope module adjusts an optimum scanning optical focal length of the linear scanning lens module with respect to the test probe card to be tested, the linear scanning lens module scans all areas data of the test probe card to be tested and stores the scanned data in the database, the operation module compares the all areas data with coordinate data in order to detect defected pins of the test probe card to be tested, the CCD microscope module processes quality of the defected pins, or the x-y axis movement platform moves the test probe card to be tested to the CCD image adjustment module for adjustment and for processing deflected pins, and these are shown on the input and output module by operating the computer.

One of the exemplary embodiments, the CCD image adjustment module comprises a central lens including a central CCD camera and a central high magnification lens; a first side lens including a first side CCD camera and a first side high magnification lens; and a second side lens including a second side CCD camera and a second side high magnification lens; wherein the central lens is oriented vertically, the first side lens is oriented obliquely to one side of the central lens, the first side high magnification lens is oblique with respect to the central high magnification lens, the second side lens is oriented obliquely to the other side of the central lens, the second side high magnification lens is oblique with respect to the central high magnification lens, and lines along lengthwise directions of the central lens, the first side lens, and the second side lens intersect at a same point.

One of the exemplary embodiments, the x-y axis movement platform comprises an x-axis sliding platform mechanism including an x-axis sliding platform, two parallel x-axis rails, a first servo motor, an x-axis reciprocating screw connected to an output of the first servo motor, a first sliding block provided on the x-axis sliding platform and configured to slide along the x-axis rails, and a first drive seat provided on the x-axis sliding platform and driven by the x-axis reciprocating screw; and a y-axis sliding platform mechanism including an y-axis sliding platform, two parallel y-axis rails fastened on the x-axis sliding platform, a second servo motor, a y-axis reciprocating screw connected to an output of the second servo motor, a second sliding block provided on the y-axis sliding platform and configured to slide along the y-axis rails, a second drive seat provided on the y-axis sliding platform and driven by the y-axis reciprocating screw.

One of the exemplary embodiments, further comprises a first z-axis movement module including a first support, a first reciprocating screw, a first servo motor, a first drive seat, a first rail, and a first sliding block wherein the first sliding block is configured to slide on the first rail, the first drive seat is provided on the first reciprocating screw so that the first drive seat is configured to move linearly in response to rotation of the first reciprocating screw, the first reciprocating screw is connected to an output of the first servo motor, both the first servo motor and the first rail are secured to the first support, and the linear scanning lens module is secured to both the first sliding block and the first drive seat; and a second z-axis movement module including a second support, a second reciprocating screw, a second servo motor, a second drive seat, a second rail, and a second sliding block wherein the second sliding block is configured to slide on the second rail, the second drive seat is provided on the second reciprocating screw so that the second drive seat is configured to move linearly in response to rotation of the second reciprocating screw, the second reciprocating screw is connected to an output of the second servo motor, both the second servo motor and the second rail are secured to the second support, and the CCD image adjustment module is secured to both the second sliding block and the second drive seat.

One of the exemplary embodiments, the CCD microscope module is secured to the linear scanning lens module so as to move in synchronism.

One of the exemplary embodiments, a horizontal setting of focal length of the CCD microscope module with respect to the test probe card to be tested is the same as that of focal length of the linear scanning lens module with respect to the test probe card to be tested.

One of the exemplary embodiments, further comprises an x-y axis optical ruler for providing location information of the test probe card to be tested to the computer so that linear scanning lens module scans and fetches images.

One of the exemplary embodiments, the input and output module is a touchscreen.

One of the exemplary embodiments, the linear scanning lens module includes an optical sensor and a high magnification linear scanning lens.

One of the exemplary embodiments, further comprises a co-axial light source in the linear scanning lens module, wherein light emitted by the co-axial light source is directed to an origin of the test probe card to be tested.

It is another object of the invention to provide a test probe card detection system comprising a linear scanning lens module; a CCD microscope module; and a coordinate file; wherein the CCD microscope module is configured to adjust and confirm a scanning optical focal length of a test probe card to be tested, the linear scanning lens module scans all areas data of the test probe card to be tested and stores the scanned all areas data in a database, and the all areas data is compared with the coordinate file in order to detect defected pins of the test probe card to be tested.

One of the exemplary embodiments, further comprises a CCD image adjustment module and a computer, wherein the CCD microscope module confirms the defected pins and obtains data of the defected pins, the data of the defected pin is sent to the CCD image adjustment module which displays same on a display of the computer so as to make an adjustment on the display of the computer and show results of the adjustment on the display of the computer.

It is a further object of the invention to provide a test probe card detection method, comprising the steps of (a) loading a coordinate file of a test probe card; (b) setting a plurality of detection conditions; (c) scanning data of all areas of the test probe card to be tested is scanned; and (d) comparing the data of all areas of the test probe card to be tested with the coordinate file in order to detect defected pins of the test probe card to be tested One of the exemplary embodiments, before step (c), a CCD microscope module adjusts and confirms an optical focal length of the test probe card to be tested, and after step (d) the CCD microscope module confirms and obtains data of the detected defected pins of the test probe card to be tested, and the data of the detected defected pins and the scanned data are sent to a CCD image adjustment module and are shown on a display.

One of the exemplary embodiments, the adjustment is done on the display or the CCD microscope module processes problems of the defected pins and shows results of the processing.

One of the exemplary embodiments, the test probe card detection method employs linear scanning.

One of the exemplary embodiments, the test probe card detection method employs a total solution to compare the data of all areas of the test probe card to be test with the coordinate file in order to calculate a minimum number of the deflected pins.

One of the exemplary embodiments, step (b) includes setting the pin to be a reflection point having a plurality of light sources, sensing reflected light when co-axial light impinges the pin of the test probe card to be tested, and obtaining light reflection ratio of the reflected light having a predetermined strength in order to determine quality of the tip of the pin.

One of the exemplary embodiments, the defected pins of the test probe card to be tested of step (d) includes pins having surface oxidation, wear, damage, and breaking; lacking of pins; and deflected pins.

The invention has the following advantages and benefits in comparison with the conventional art:

The invention scans the test probe card in one time and stores the scanned data. Further, the invention compares the data of all areas of the test probe card with the coordinate file in order to quickly finish detection. Detection time of the test probe card is about 2 minutes and this is a great reduction in comparison with about 40 minutes of the conventional art.

Four points positioning of the conventional art is not employed by the invention. Hence, movement error does not distribute to each pin and the error is not accumulated to any subsequent comparisons. Therefore, the test results are correct and have high precision.

The detection and comparison of the invention are automatic with no manual search and positioning. It is time saving and labor saving. It does not depend upon the feeling of the employee operating the device as experienced by the conventional art. Moreover, the adjustment can be made by operating the computer by watching results on the display of the computer. It is not only correct but also has increased precision with respect to a repeated detection and comparison of the same point.

The invention can detect not only deflected pins but also items not detected by the conventional art. The items include pins having surface oxidation, wear, damage, and breaking; lacking of pins; and deflected pins.

Locations of defected pins detected by the invention can be shown on the display. Further, any pins can be selected on a coordinate for highlighting purposes. The pin can be assigned a serial number so as to be positioned for fetching images for analysis. It is possible of solving problems on the display. It is very convenient.

The above and other objects, features and advantages of the invention will become apparent from the following detailed description taken with the accompanying drawings.

DETAILED DESCRIPTION OF THE INVENTION

Figure 1:
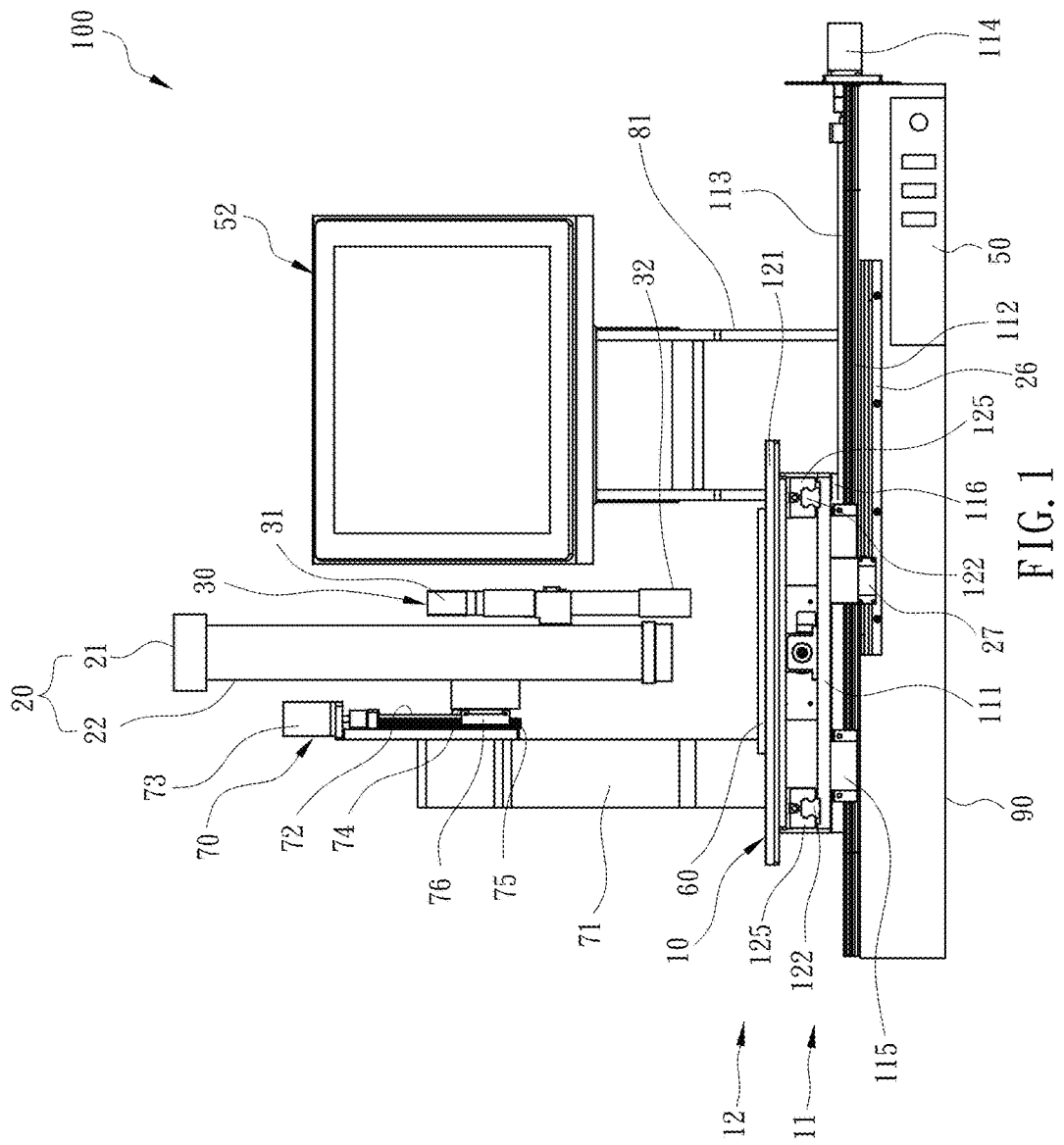
FIG. 1 is a front view of a test probe card detection system according to the invention.
Figure 2:
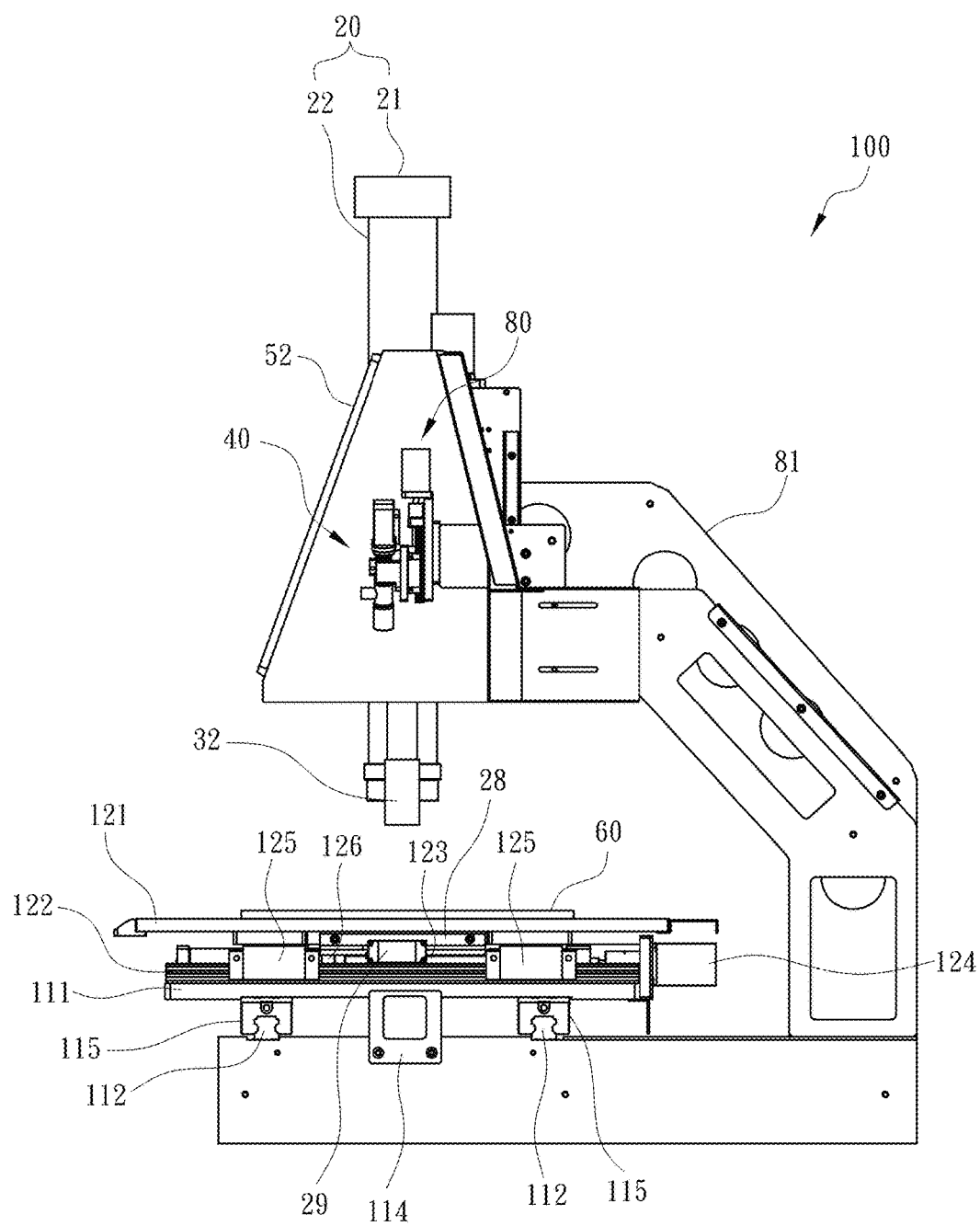
FIG. 2 is a left side view of FIG. 1.
Figure 3:
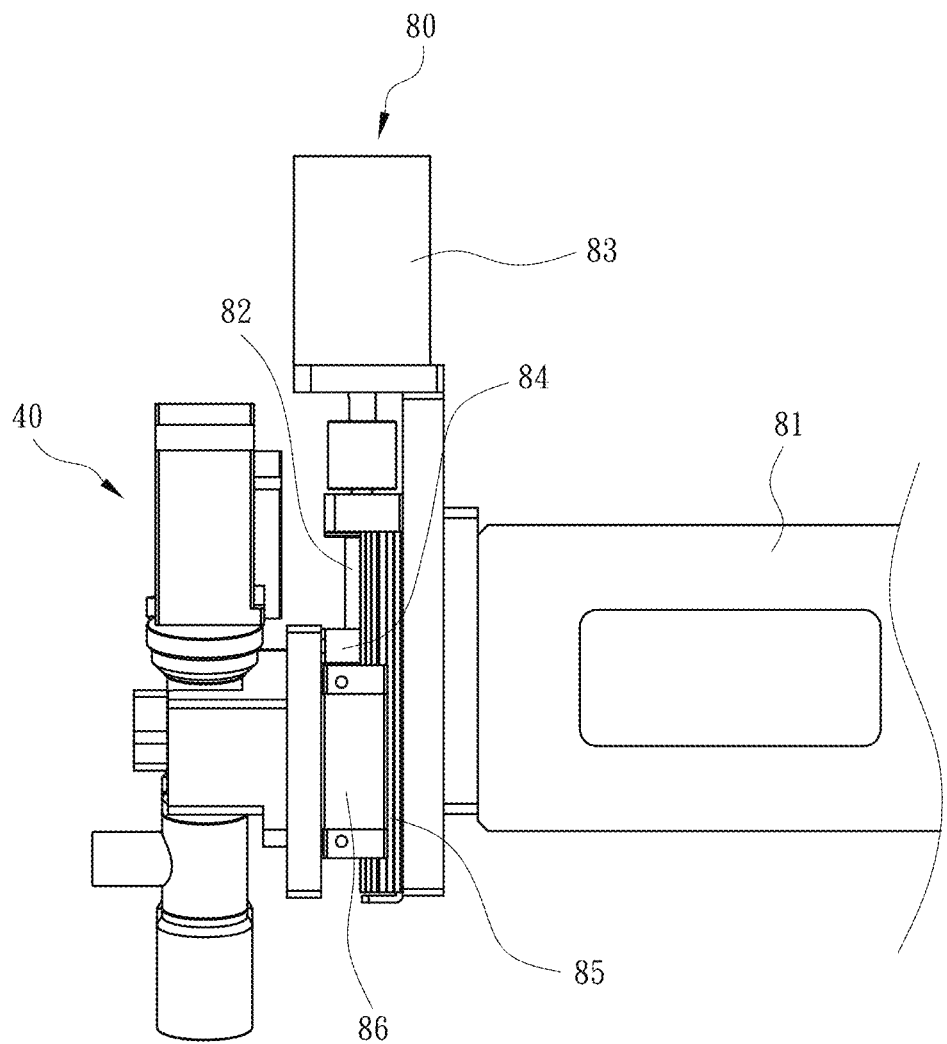
FIG. 3 is a side elevation of the CCD image adjustment module and the second z-axis movement module.
Figure 4:
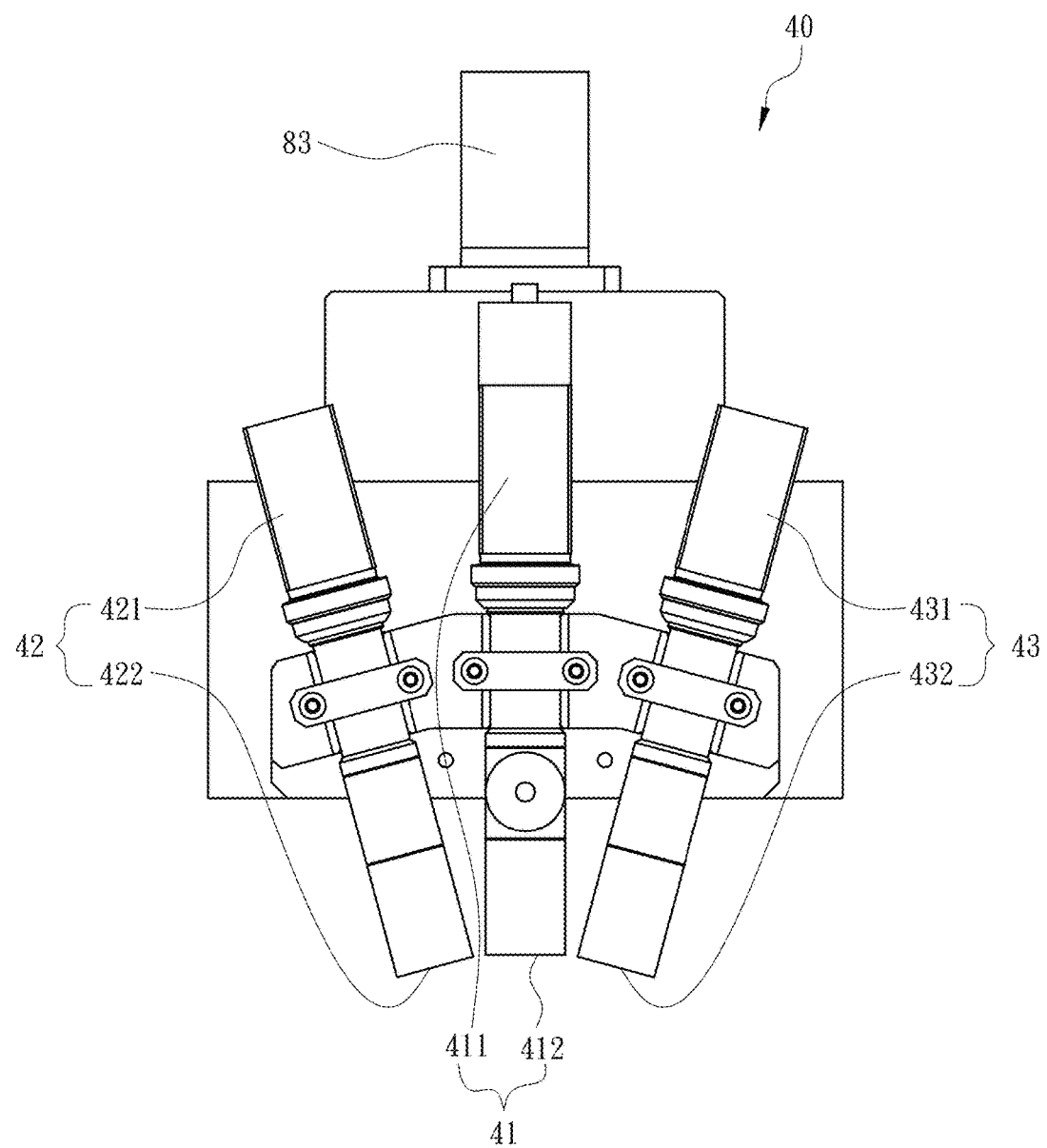
FIG. 4 is a front view of FIG. 3.

Embodiments of the invention will now be described, by way of example only, with reference to the accompanying drawings.

Referring to FIGS. 1 to 5, a test probe card detection system in accordance with the disclosed example comprises an x-y axis movement platform 10, a linear scanning lens module 20, a CCD (charge-coupled device) microscope module 30, a CCD image adjustment module 40, a computer 50, a first z-axis movement module 70, and a second z-axis movement module 80 discussed in detail below.

In one embodiment, the x-y axis movement platform 10 may move in Cartesian coordinates (x, y), and a test probe card 60 to be tested is placed on the x-y axis movement platform 10.

In one embodiment, the x-y axis movement platform 10 includes an x-axis sliding platform mechanism 11 and a y-axis sliding platform mechanism 12. The x-axis sliding platform mechanism 11 includes an x-axis sliding platform 111, two parallel x-axis rails 112, an x-axis reciprocating screw 113 and a servo motor 114. A sliding block 115 is provided on the x-axis sliding platform 111 and may slide along the x-axis rails 112. A drive seat 116 is provided on the x-axis sliding platform 111 and is driven by the x-axis reciprocating screw 113. The x-axis reciprocating screw 113 is connected to an output of the servo motor 114.

In one embodiment, the y-axis sliding platform mechanism 12 includes a y-axis sliding platform 121, two parallel y-axis rails 122, a y-axis reciprocating screw 123 and a servo motor 124. A sliding block 125 is provided on the y-axis sliding platform 121 and may slide along the y-axis rails 122. A drive seat 126 is provided on the y-axis sliding platform 121 and is driven by the y-axis reciprocating screw 123. The y-axis reciprocating screw 123 is connected to an output of the servo motor 124. The y-axis rails 122 are fastened on the x-axis sliding platform 111.

The servo motor 124 activates to rotate the y-axis reciprocating screw 123 which in turn move the drive seat 126 so that the y-axis sliding platform 121 may move along the y-axis rails 122. Likewise, the servo motor 114 activates to rotate the x-axis reciprocating screw 113 which in turn move the drive seat 116 so that the x-axis sliding platform 111 may move along the x-axis rails 112.

A test probe card 60 to be tested is placed on the y-axis sliding platform 121 of the x-y axis movement platform 10. The test probe card 60 to be tested may move in Cartesian coordinates (x, y) on the x-y axis movement platform 10. The test probe card 60 to be tested is secured to the y-axis sliding platform 121 by means of fasteners. But this is known in the art and thus a detailed description thereof is omitted herein for the sake of brevity.

In any embodiment, the linear scanning lens module 20 is above the x-y axis movement platform 10 in movement. Further, the linear scanning lens module 20 may move along z-axis in a three dimensional Cartesian coordinate system. The linear scanning lens module 20 obtains image data of all area of the test probe card 60 to be tested by scanning. The linear scanning lens module 20 includes an optical sensor 21 and a high magnification linear scanning lens 22. A co-axial light source is provided in the linear scanning lens module 20. Light emitted by the co-axial light source is directed to an origin (not shown) of the test probe card 60 to be tested.

In one embodiment, the CCD microscope module 30 is above the x-y axis movement platform 10 in movement. Further, the CCD microscope module 30 may move along z-axis in a three dimensional Cartesian coordinate system. The CCD microscope module 30 includes a digital camera 31 and a microscope objective lens 32.

In one embodiment, the CCD image adjustment module 40 is above the x-y axis movement platform 10 in movement. The CCD image adjustment module 40 includes a central lens 41, a first side lens 42, and a second side lens 43. The central lens 41 is oriented vertically and includes a central CCD camera 411 and a central high magnification lens 412. The first side lens 42 includes a first side CCD camera 421 and a first side high magnification lens 422. The first side lens 42 is oriented obliquely to the left of the central lens 41. The first side high magnification lens 422 is oblique with respect to the central high magnification lens 412. The second side lens 43 includes a second side CCD camera 431 and a second side high magnification lens 432. The second side lens 43 is oriented obliquely to the right of the central lens 41. The second side high magnification lens 432 is oblique with respect to the central high magnification lens 412. The lines along the lengthwise directions of the central lens 41, the first side lens 42, and the second side lens 43 intersect at the same point. In the embodiment, an angle between the first side lens 42 and the second side lens 43 is 180 degrees. In fact, the angle can be 45 degrees, 90 degrees, or any appropriate degrees.

The central lens 41 can see images of the front of an object, and each of the first and second side lenses 42 and 43 can see images of the side and shaded areas. The CCD image adjustment module 40, comprising the central lens 41, the first side lens 42, and the second side lens 43, can obtain an image of more perspective rather than a two dimensional image. As a result, the CCD image adjustment module 40 can see details of the tip of a pin such as oxidation, wear and damage, and broken pins.

In one embodiment, the first z-axis movement module 70 includes a support 71, a reciprocating screw 72, a servo motor 73, a drive seat 74, a rail 75 and a sliding block 76. The sliding block 76 may slide on the rail 75. The drive seat 74 is provided on the reciprocating screw 72 so that the drive seat 74 may move linearly in response to rotation of the reciprocating screw 72. The reciprocating screw 72 is connected to an output of the servo motor 73. The servo motor 73 and the rail 75 are secured to the support 71. The linear scanning lens module 20 is secured to both the sliding block 76 and the drive seat 74. The reciprocating screw 72 rotates in response to activation of the servo motor 73. And in turn, the drive seat 74 moves upward and then downward repeatedly. Further, the linear scanning lens module 20 moves along the rail 75 in z-axis.

Additionally, in one embodiment, the CCD microscope module 30 and the linear scanning lens module 20 are secured together so that they can move in synchronism. In other words, the CCD microscope module 30 moves in response to movement of the linear scanning lens module 20. In one embodiment, a horizontal setting of focal length of the linear scanning lens module 20 with respect to the test probe card 60 to be tested is the same as that of the CCD microscope module 30 with respect to the test probe card 60 to be tested.

In one embodiment, the second z-axis movement module 80 includes a support 81, a reciprocating screw 82, a servo motor 83, a drive seat 84, a rail 85 and a sliding block 86. The sliding block 86 may slide on the rail 85. The drive seat 84 is provided on the reciprocating screw 82 so that the drive seat 84 may move linearly in response to rotation of the reciprocating screw 82. The reciprocating screw 82 is connected to an output of the servo motor 83. The servo motor 83 and the rail 85 are secured to the support 81. The CCD image adjustment module 40 is secured to both the sliding block 86 and the drive seat 84. The reciprocating screw 82 rotates in response to activation of the servo motor 83. And in turn, the drive seat 84 moves upward and then downward repeatedly. Further, the CCD image adjustment module 40 moves along the rail 85 in z-axis.

Figure 5:
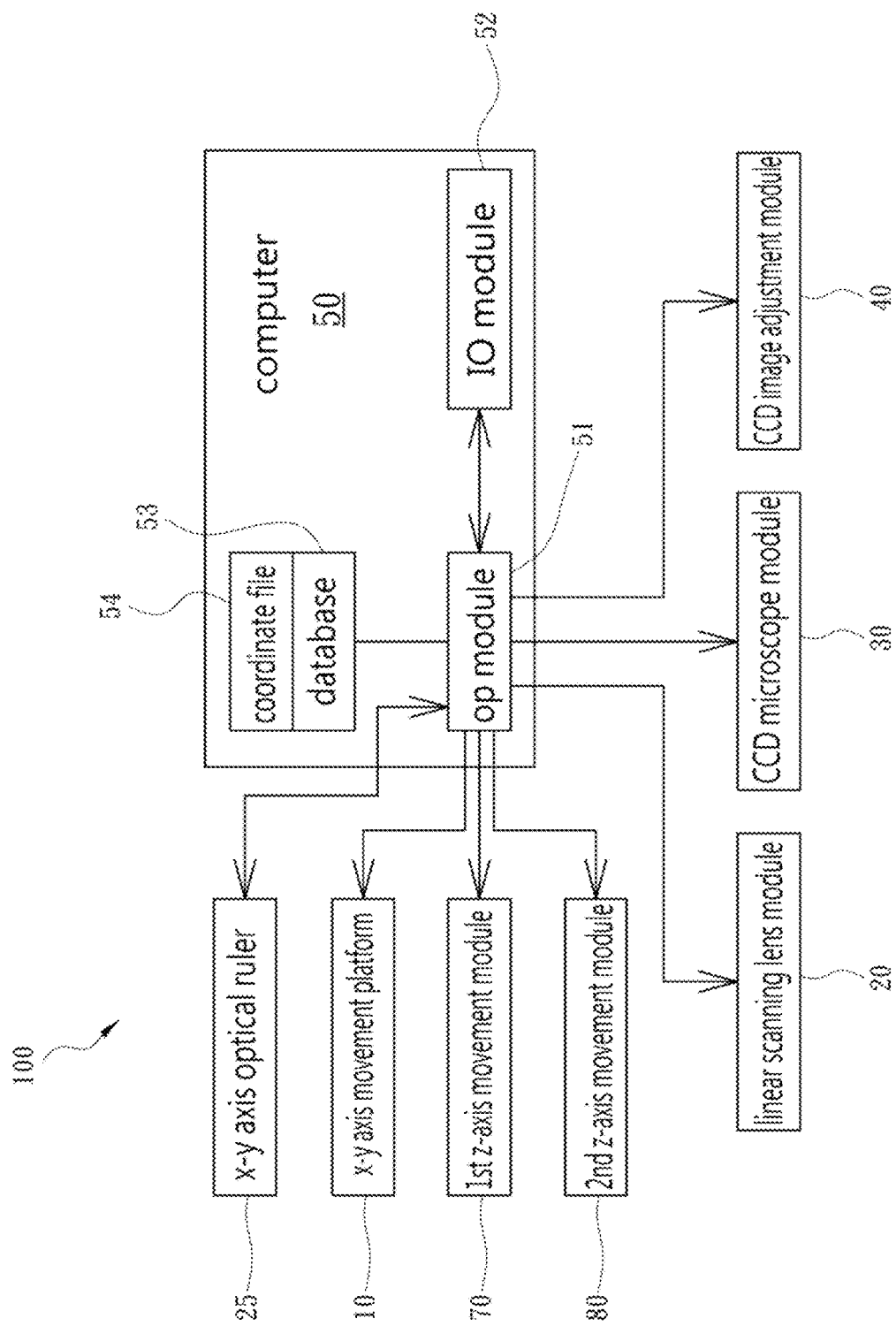
FIG. 5 is a block diagram of the test probe card detection system according to the invention.

As shown in FIG. 5, in one embodiment, the computer 50 includes an operation module 51, an input and output module 52 and a database 53 for storing data including data of a test probe card coordinate file 54. The input and output module 52 can input instructions and output graphic and text files. The operation module 51 can process input and output information.

In the embodiment, the input and output module 52 is a touchscreen, i.e., a display having input and output functions. In another embodiment, the input and output module 52 is implemented as another devices, such as a display and a keyboard (both not shown).

In one embodiment, the input and output module 52 includes an x-y axis optical ruler 25 for providing location information of the test probe card 60 to be tested to the computer 50. The computer 50 further comprises an x-axis optical ruler 26 having a read head 27. In the embodiment, the x-axis optical ruler 26 is secured to a base 90 and the read head 27 may move in response to movement of the sliding block 115. The x-axis optical ruler 26 provides signals to the linear scanning lens module 20 so that the linear scanning lens module 20 can take consecutive images in equal spacing. A y-axis optical ruler 28 has a read head 29. In one embodiment, the read head 29 is stationary and the y-axis optical ruler 28 may move in response to movement of the sliding block 125. Location signals of the y-axis optical ruler 28 provide information of each scanned location. The information of all scanned locations is combined to form complete x-y axis location information. In one embodiment, the base 90 of the disclosed example is provided for mounting all other components described above.

Use and operation of the disclosed example are described in detail below.

In use, the test probe card 60 to be tested is provided and secured to the x-y axis movement platform 10. The computer 50 controls the x-y axis movement platform 10 to move the test probe card 60 to be tested. The CCD microscope module 30 adjusts an optimum scanning optical focal length of the linear scanning lens module 20 with respect to the test probe card 60 to be tested. The x-y axis optical ruler 25 provides location information of the test probe card 60 to be tested to the computer 50. The linear scanning lens module 20 scans all areas data of the test probe card 60 to be tested and stores the scanned data in the database 53. The operation module 51 compares the all areas data with coordinate data in order to detect defected pins of the test probe card 60 to be tested. The defected pins include deflected pins and pins having unacceptable quality such as oxidation, wear, damage of the tip of the pin and broken pins. Data of the defected pins is stored in the database 53.

The CCD microscope module 30 processes quality of pins. The x-y axis movement platform 10 moves the test probe card 60 to be tested to the CCD image adjustment module 40 for adjustment and for processing deflected pins. Above can be shown by operating the computer 50. In detection, the all areas data is compared with coordinate data in order to calculate a minimum number of deflected pins. After detecting a defected pin, the CCD microscope module 30 confirms and obtains data of the defected pin. The input and output module 52 then shows it on the screen. Thus, the problem of the defected pin can be solved by operating the computer 50 by watching changes on the screen. Alternatively, the test probe card 60 to be tested is moved to the CCD image adjustment module 40 and data already obtained by the CCD microscope module 30 is shown on the screen of the input and output module 52. Therefore, it is possible of performing adjustment of pin by watching changes on the screen.

Figure 6:
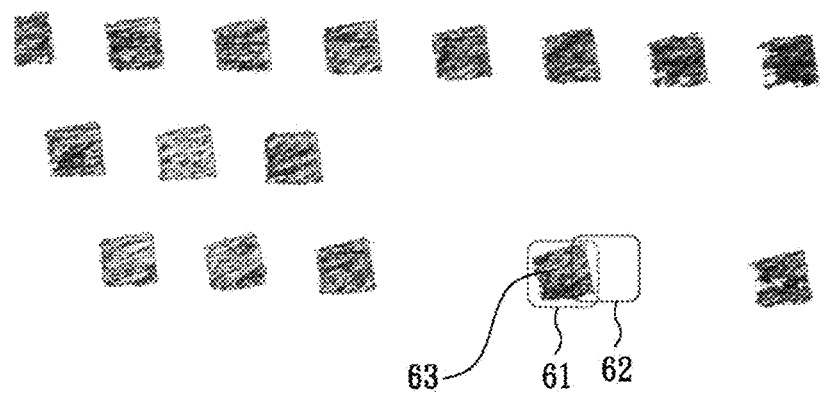
FIGS. 6 and 7 schematically show steps of adjusting pins on the screen of a computer respectively.
Figure 7:
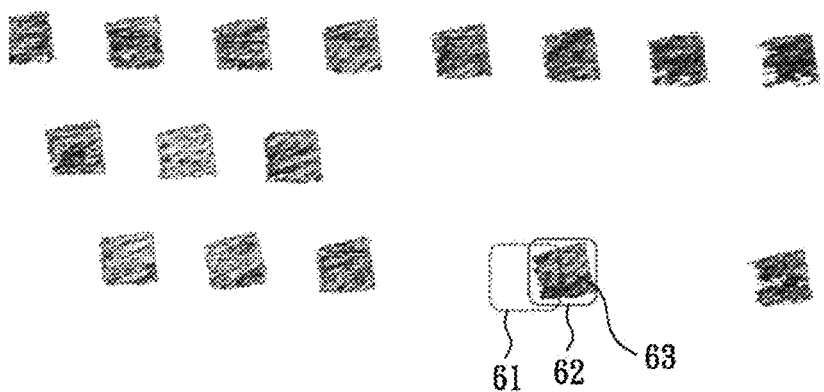

Referring to FIGS. 6 and 7, they schematically depict adjustment of a pin. In FIG. 6, the frame 61 shown in dotted lines represents a deflected location of a pin 63 and the frame 62 shown in line represents the correct location of the pin 63. In adjustment, conventional tools can be operated to adjust the pin 63 to its correct location. In FIG. 7, it shows the pin 63 has been adjusted to its correct location.

Further, the pin of the test probe card 60 to be tested is set to be a reflection point having a plurality of light sources by the disclosed example. The optical sensor 21 of the linear scanning lens module 20 may sense the reflected light when co-axial light impinges the test probe card 60 to be tested. Information of the sensed light is processed by the operation module 51 of the computer 50 in order to obtain light reflection ratio of reflected light having a desired strength. Thereafter, quality of the tip of the pin can be determined and shown on the screen. Hence, it can be processed conveniently, quickly.

Problems of the tip of the pin detected by the disclosed example include surface oxidation, wear, damage and breaking of the pin and lacking of pins.

Further, the pin of the test probe card 60 to be tested is set to be a reflection point having a plurality of light sources by the disclosed example. The optical sensor 21 of the linear scanning lens module 20 may sense the reflected light when co-axial light impinges the test probe card 60 to be tested. Information of the sensed light is processed by the operation module 51 of the computer 50 in order to obtain light reflection ratio of reflected light having a desired strength. Thereafter, quality of the tip of the pin can be determined and shown on the screen. Hence, it can be processed conveniently, quickly. Problems of the tip of the pin detected by the disclosed example include surface oxidation, wear, damage and breaking of the pin and lacking of pins.

Further, the pin of the test probe card 60 to be tested is set to be a reflection point having a plurality of light sources by the disclosed example. The optical sensor 21 of the linear scanning lens module 20 may sense the reflected light when co-axial light impinges the test probe card 60 to be tested. Information of the sensed light is processed by the operation module 51 of the computer 50 in order to obtain light reflection ratio of reflected light having a desired strength. Thereafter, quality of the tip of the pin can be determined and shown on the screen. Hence, it can be processed conveniently, quickly.

Figure 8:
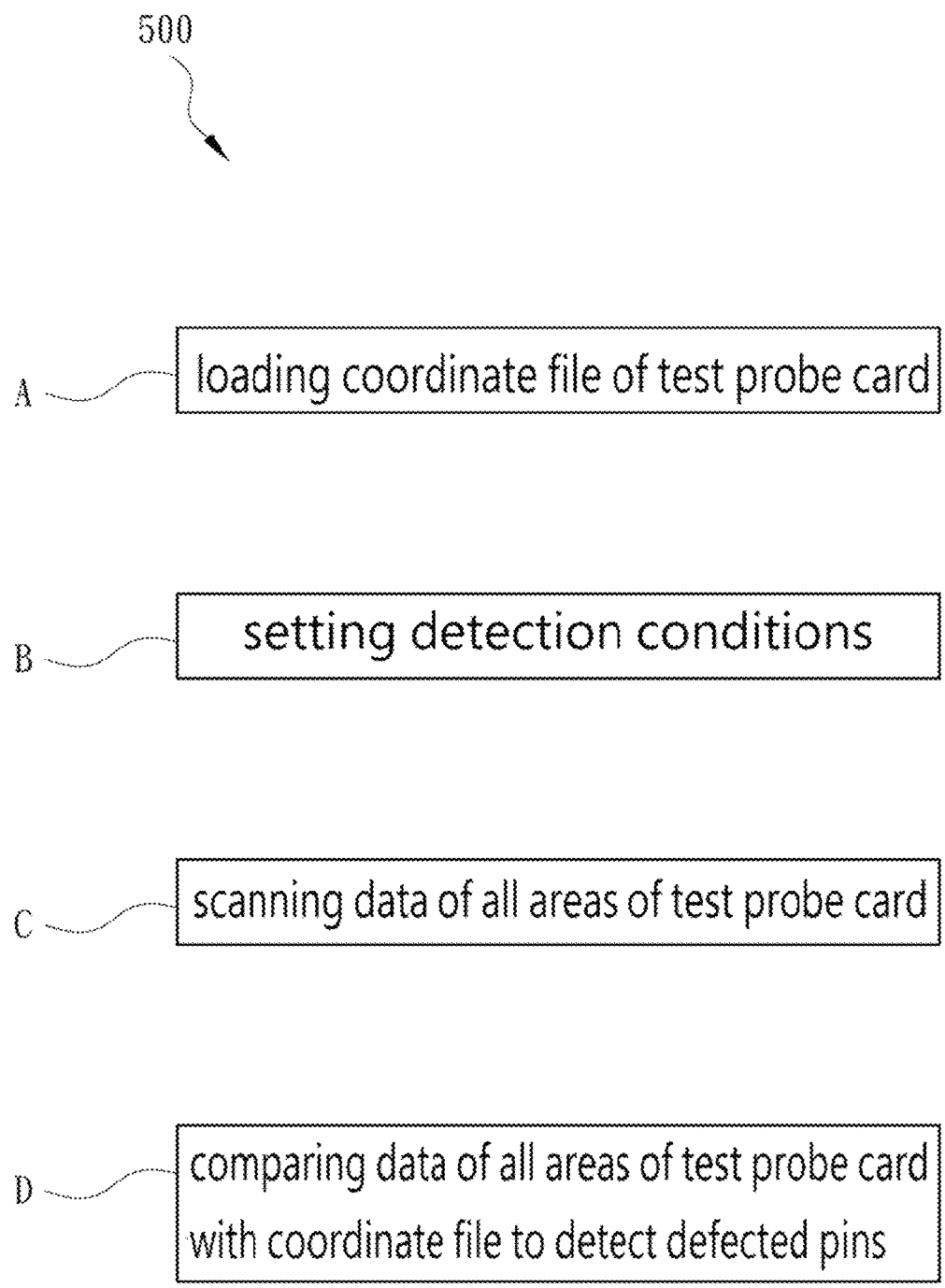
FIG. 8 is a flow chart of a test probe card detection method according to the invention.

Referring to FIG. 8, it is a flow chart of a test probe card detection method 500 according to an embodiment. The method 500 can detect quality of the tip of a test probe card and deflected pin. The method 500 comprises a number of steps for description purpose. But, the method 500 is not limited to the described steps. For example, some steps may depart from the description by being performed in a different sequence or simultaneously. The described steps may be not performed in one or more embodiments. Further, the described steps may be performed in one or more independent steps or stages.

In step A, a coordinate file of a test probe card is loaded. The coordinate file of the test probe card should be prepared in advance and stored in a database of the computer 50.

In step B, detection conditions are set. The detection conditions include deflected pin and/or quality of the tip of a pin. Distribution of the defects is also set.

In step C, data of all areas of the test probe card 60 to be tested is scanned. The linear scanning lens module 20 is used to perform a linear scan so as to digitize the data of the all areas of the test probe card 60 to be tested. Prior to scanning, the CCD microscope module 30 is used to adjust and confirm an optical focal length of the test probe card to be tested.

In step D, the data of all areas of the test probe card 60 to be tested is compared with the coordinate file in order to detect defected pins. After detection, the CCD microscope module 30 confirms and obtains data of the detected defected pins. The data and the scanned data are sent to the CCD image adjustment module 40 and shown on the screen of a display. Adjustment of the pin can be shown on the screen of the display. Also, results of the adjustment are shown on the screen of the display. The method 500 employs a total solution to compare the data of all areas of the test probe card with the coordinate file in order to calculate a minimum number of deflected pins.

Further, the method 500 includes setting the pin to be a reflection point having a plurality of light sources. The reflected light is sensed when co-axial light impinges the pin of the test probe card 60 to be tested. Therefore, light reflection ratio of reflected light having a desired strength is obtained in order to determine quality of the tip of the pin.

In the method 500, the following are further included: All defected pins are shown on the coordinate. Any pin can be selected to show its conditions such as deflection, lacking of pins, surface of pin oxidation, wear and damage, and breaking. The pin can be assigned a serial number so as to be positioned for fetching images for analysis.

While the invention has been described in terms of preferred embodiments, those skilled in the art will recognize that the invention can be practiced with modifications within the spirit and scope of the appended claims.

What is claimed is:

1. A test probe card detection system for detecting a test probe card, comprising:

an x-y axis movement platform configured to move in Cartesian coordinates (x, y), the x-y axis movement platform comprising an x-axis sliding platform mechanism and a y-axis sliding platform mechanism, the x-axis sliding platform mechanism including an x-axis sliding platform, two parallel x-axis rails, a first servo motor, an x-axis reciprocating screw connected to an output of the first servo motor, a first sliding block provided on the x-axis sliding platform and configured to slide along the x-axis rails, and a first drive seat provided on the x-axis sliding platform and driven by the x-axis reciprocating screw, the y-axis sliding platform mechanism including an y-axis sliding platform, two parallel y-axis rails fastened on the x-axis sliding platform, a second servo motor, a y-axis reciprocating screw connected to an output of the second servo motor, a second sliding block provided on the y-axis sliding platform and configured to slide along the y-axis rails, a second drive seat provided on the y-axis sliding platform and driven by the y-axis reciprocating screw, and the test probe card being placed on the y-axis sliding platform;

a linear scanning lens module disposed above the x-y axis movement platform in movement, the linear scanning lens module configured to move along z-axis in a three-dimensional Cartesian coordinate system, and the linear scanning lens module configured to obtain image data of all area of the test probe card to be tested by scanning;

a CCD microscope module disposed above the x-y axis movement platform in movement, the CCD microscope module configured to move along z-axis in the three-dimensional Cartesian coordinate system;

a CCD image adjustment module disposed above the x-y axis movement platform in movement, the CCD image adjustment module configured to move along z-axis in the three-dimensional Cartesian coordinate system; and a computer including an operation module, an input and output module, and a database wherein the database is configured to store data including data of a test probe card coordinate file, the input and output module is configured to input instructions and output graphic and text files, and the operation module is configured to process input and output information;

wherein the computer controls the x-y axis movement platform to move the test probe card to be tested, the CCD microscope module adjusts an optimum scanning optical focal length of the linear scanning lens module with respect to the test probe card to be tested, the linear scanning lens module scans all areas data of the test probe card to be tested and stores the scanned data in the database, the operation module compares the all areas data with coordinate data in order to detect defected pins of the test probe card to be tested, the CCD microscope module processes quality of the defected pins, or the x-y axis movement platform moves the test probe card to be tested to the CCD image adjustment module for adjustment and for processing deflected pins, and these are shown on the input and output module by operating the computer.

2. The test probe card detection system as claimed in claim 1, wherein the CCD image adjustment module comprises:

a central lens including a central CCD camera and a central high magnification lens;

a first side lens including a first side CCD camera and a first side high magnification lens; and a second side lens including a second side CCD camera and a second side high magnification lens;

wherein the central lens is oriented vertically, the first side lens is oriented obliquely to one side of the central lens, the first side high magnification lens is oblique with respect to the central high magnification lens, the second side lens is oriented obliquely to the other side of the central lens, the second side high magnification lens is oblique with respect to the central high magnification lens, and lines along lengthwise directions of the central lens, the first side lens, and the second side lens intersect at a same point.

3. The test probe card detection system as claimed in claim 1, further comprising:

a first z-axis movement module including a first support, a first reciprocating screw, a first servo motor, a first drive seat, a first rail, and a first sliding block wherein the first sliding block is configured to slide on the first rail, the first drive seat is provided on the first reciprocating screw so that the first drive seat is configured to move linearly in response to rotation of the first reciprocating screw, the first reciprocating screw is connected to an output of the first servo motor, both the first servo motor and the first rail are secured to the first support, and the linear scanning lens module is secured to both the first sliding block and the first drive seat; and a second z-axis movement module including a second support, a second reciprocating screw, a second servo motor, a second drive seat, a second rail, and a second sliding block wherein the second sliding block is configured to slide on the second rail, the second drive seat is provided on the second reciprocating screw so that the second drive seat is configured to move linearly in response to rotation of the second reciprocating screw, the second reciprocating screw is connected to an output of the second servo motor, both the second servo motor and the second rail are secured to the second support, and the CCD image adjustment module is secured to both the second sliding block and the second drive seat.

4. The test probe card detection system as claimed in claim 3, wherein the CCD microscope module is secured to the linear scanning lens module so as to move in synchronism.

5. The test probe card detection system as claimed in claim 4, wherein a horizontal setting of focal length of the CCD microscope module with respect to the test probe card to be tested is the same as that of focal length of the linear scanning lens module with respect to the test probe card to be tested.

6. The test probe card detection system as claimed in claim 1, further comprising an x-y axis optical ruler for providing location information of the test probe card to be tested to the computer so that linear scanning lens module scans and fetches images.

7. The test probe card detection system as claimed in claim 1, wherein the input and output module is a touchscreen.

8. The test probe card detection system as claimed in claim 1, wherein the linear scanning lens module includes an optical sensor and a high magnification linear scanning lens.

9. The test probe card detection system as claimed in claim 8, further comprising a co-axial light source in the linear scanning lens module, wherein light emitted by the co-axial light source is directed to an origin of the test probe card to be tested.

* * * * *